(12) United States Patent
Hiler, II et al.

(10) Patent No.: US 6,555,681 B1
(45) Date of Patent: Apr. 29, 2003

(54) PROCESS FOR PREPARING CROSS-BRIDGED TETRAAZA MACROCYCLES

(75) Inventors: George Douglas Hiler, II, Harrison, OH (US); Christopher Mark Perkins, Cincinnati, OH (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/831,788

(22) PCT Filed: Nov. 9, 1999

(86) PCT No.: PCT/US99/26540

§ 371 (c)(1),
(2), (4) Date: May 14, 2001

(87) PCT Pub. No.: WO00/29413

PCT Pub. Date: May 25, 2000

Related U.S. Application Data

(60) Provisional application No. 60/108,380, filed on Nov. 13, 1998, now abandoned.

(51) Int. Cl.[7] ............................................. C07D 487/00
(52) U.S. Cl. ...................................................... 540/472
(58) Field of Search ......................................... 540/472

(56) References Cited

FOREIGN PATENT DOCUMENTS

| WO | WO 98/39098 A1 | 9/1998 |
|---|---|---|
| WO | WO 98/39335 A1 | 9/1998 |

*Primary Examiner*—Brenda Coleman
(74) *Attorney, Agent, or Firm*—James F. McBride; Kim W. Zerby; Steve W. Miller

(57) ABSTRACT

The present invention relates to a process for preparing a cross-bridged tetraaza macrocyclic ligands having formula (I), wherein each R is independently $C_1$–$C_{22}$ linear alkyl, $C_1$–$C_{22}$ branched alkyl, $C_7$–$C_{22}$ alkylenearyl, $C_8$–$C_{22}$ alkyl substituted alkylenearyl, and mixtures thereof; each index n is independently from 0 to 3, by contacting the a di-quaternary cis tetracycle precursor with as little as one equivalent of a borohydride reducing agent. The present process eliminates the need to use up to a twenty fold excess of reducing agent thereby further eliminating the need for work-up conditions which liberate significant amounts of hydrogen gas and which requires the disposal of large amounts of boron waste products.

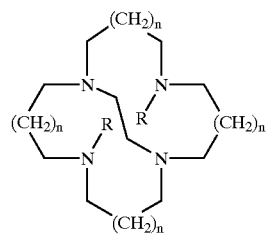

(I)

14 Claims, No Drawings

PROCESS FOR PREPARING CROSS-BRIDGED TETRAAZA MACROCYCLES

CROSS REFERENCE TO RELATED APPLICATIONS

This application is a national stage entry under 35 U.S.C. § 371 of PCT/US99/26540, filed Nov. 9, 1999, which claims the benefit of U.S. Provisional Application No. 60/108,380 filed Nov. 13, 1998 (now abandoned).

FIELD OF THE INVENTION

The present invention relates to an improved process for preparing cross-bridged tetraaza macrocycles, said macrocycles suitable as ligands for use in preparing transition metal complexes. The present invention provides a process which is well suited for use in industrial and other commercial preparations of the herein described crossed-bridged macrocycles.

BACKGROUND OF THE INVENTION

Tetraaza macrocyclics, for example, cyclam, have been prepared in numerous ways, however, there is a paucity of information relating to the preparation of cross-bridged tetraaza macrocyclics inter alia 1,5,8,12-tertaaza-bicyclo[6.6.2]hexadecane. Recently, bis N-substituted tetraaza macrocyclics inter alia 5,12 dialkyl or dialkylenearyl 1,5,8,12-tetraaza-bicyclo[6.6.2]hexadecanes have found wide applicability as ligands especially in the area of transition metal catalysts inter alia bleach catalysts.

WO 98/39335 A1 "Improved Methods of Making Cross-Bridged Macropoly-cycles" discloses a rational procedure for preparing cross bridged macropolycyclic ligands which is amenable to high yields necessary for industrial scale-up. However, the reductive ring cleavage step which results in bicyclo bridged-ring formation utilizes a large excess of a borohydride reducing agent. This excess of reducing agent can place constraints on the formulator. For example, when manufacturing the disclosed ligands on a industrial scale, any excess of reagent beyond the stoichiometric amount places an increased cost burden on the formulator. In addition, the proper recovery and disposal of boron waste products adds cost to the process. Excess borohydride requires neutralization which involves the use of acid and the evolution of large quantities of hydrogen gas.

Therefore, a need exists for a highly quantitative, stoichiometric process for preparing cross-bridged macropolycyclic ligands.

SUMMARY OF THE INVENTION

The present invention meets the aforementioned needs in that it has been surprisingly discovered that approximately one mole equivalent of a borohydride reducing agent is necessary to convert cis-tetracycles to cross bridged macropolycyclic ligands.

A first aspect of the present invention relates to a process for preparing a cross-bridged tetraaza macrocyclic ligand having the formula:

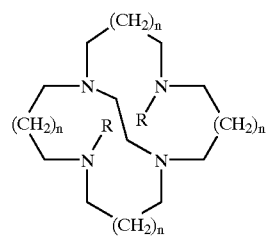

wherein each R is independently $C_1$–$C_{22}$ linear alkyl, $C_1$–$C_{22}$ branched alkyl, $C_7$–$C_{22}$ alkylenearyl, $C_8$–$C_{22}$ alkyl substituted alkylenearyl, and mixtures thereof; each index n is independently from 0 to 3, said process comprising the steps of:

a) reacting one mole equivalent of a tetraaza macrocyclic ligand precursor having the formula:

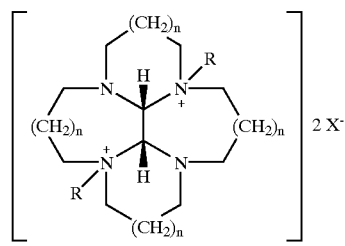

wherein $X^-$ is an anion which provides charge neutrality, with from about 1 mole equivalent to about 3.5 mole equivalents of a reducing agent having the formula $MBH_4$ wherein M is selected from the group consisting of lithium, sodium, potassium, and mixtures thereof; at a pH of at least about 11 to form a macrocyclic ligand; and b) optionally isolating said macrocyclic ligand.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

Until the disclosure of WO 98/39335 A1 there was no process for preparing cross-bridged tetraaza macrocyclic ligands, especially ligands suitable for use in preparing catalysts inter alia manganese (II) bleach catalysts, which was suitable for industrial application.

WO 98/39098 A1 "Catalysts and Methods for Catalytic Oxidation" published Sep. 11, 1998 discloses cross-bridged tetraaza macrocyclic ligands and transition metal complexes formed therefrom. These transition metal complexes serve as oxidation catalysts which have a wide range of uses inter alia as bleaching catalysts for use in removing stains from fabric. A preferred catalyst is 5,12-dimethyl-1,5,8,12-tertaaza-bicyclo[6.6.2]hexadecane manganese (II) chloride which comprises the cross-bridged ligand 5,12-dimethyl-1,5,8,12-tertaaza-bicyclo[6.6.2]hexadecane. WO 98/39335 A1 describes the preparation of this ligand wherein 12 moles of $NaBH_4$ is used to cleave a bis(quaternary-N-methyl) cis-tetracycle precursor to 5,12-dimethyl-1,5,8,12-tertaaza-bicyclo[6.6.2]hexadecane. The present invention stabilizes the borohydride by conducting the step (a) at a pH of at least about 11.

It has been surprisingly discovered that this transformation and transformations which convert other cis-tetracycles to cross-bridged macrocycles can be conducted in nearly quantitative yield with a near stoichiometric amount of borohydride reducing agent.

The process of the present invention relates to the reductive cleavage of a cis-tetracycle having the formula:

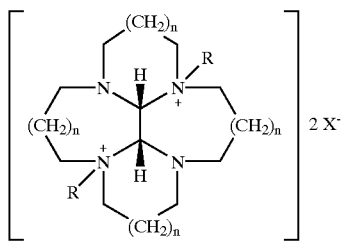

wherein each R is independently $C_1$–$C_{22}$ linear alkyl, $C_1$–$C_{22}$ branched alkyl, $C_7$–$C_{22}$ alkylenearyl, $C_8$–$C_{22}$ alkyl substituted alkylenearyl, and mixtures thereof; X represents an anion which provides electronic neutrality; each index n is independently from 0 to 3. The reductive ring cleavage results in a tetraaza macrocyclic ligand having the formula:

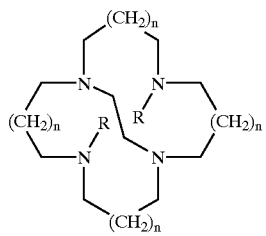

wherein R and the index n are the same as defined herein above.

X is an anion which serves to provide electronic neutrality to the bis-quaternary cis tetracycle. Those of ordinary skill in the art recognize that the term "electronic neutrality" refers to "a sufficient amount of an anionic species which satisfies the molecular charge balance requirements" and that a mixture of mono-, di-, tri-, etc. electronic species may be use herein. X preferably has unit negative charge, for example, halogen, tosylate methylsulfate. However, X may have more than one negative charge, for example, sulfate, in which case the formulator requires only half the amount necessary when using a unit negative-charged anion.

For the purposes of the present invention the term "linear alkyl" is defined as "any linear alkyl chain" non-limiting examples of which include methyl, ethyl, n-propyl, n-decyl, etc. For the purposes of the present invention the term "branched alkyl" is defined herein as "any alkyl chain which has one or more alkyl branches" non-limiting examples of which included, 2-ethylhexyl, 3-methylpentyl, isopropyl, isobutyl, etc. For the purposes of the present invention the term "alkylenearyl" is defined as a unit having the formula:

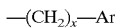
—$(CH_2)_x$—Ar wherein Ar represents an aromatic moiety having from 6 to 14 carbon atoms and x has the value from 1 to 16. Non-limiting examples of Ar units are phenyl and naphthyl. For the purposes of the present invention the term "alkyl substituted alkylenearyl" is defined as "an alkylenearyl unit wherein one or more carbons atoms of the Ar unit has an alkyl unit replacing the hydrogen atom." Non-limiting examples of alkyl substituted alkylenearyl Ar units include 4-methylphenyl (toluyl) and 3,5-di-tert-butylphenyl. For alkyl substituted alkylenearyl units the index x is from 1 to 15.

In its basic form, the process of the present invention comprises a reduction step and an optional isolation and/or purification step. The reduction step is necessary in that the required chemical transformation is performed in this step, however, the isolation and/or purification step is optional. The formulator may find that isolation of the cross-bridged macrocycle is not a necessary step if the next usage of the formed ligand is, for example, formation of a metal complex, and this succeeding step can be successfully performed on the crude, un-isolated product which is still in the reduction step admixture.

STEP (a) Reductive Cleavage

Step (a) comprises the borohydride ($BH_4^-$) reductive cleavage as outlined in the following scheme:

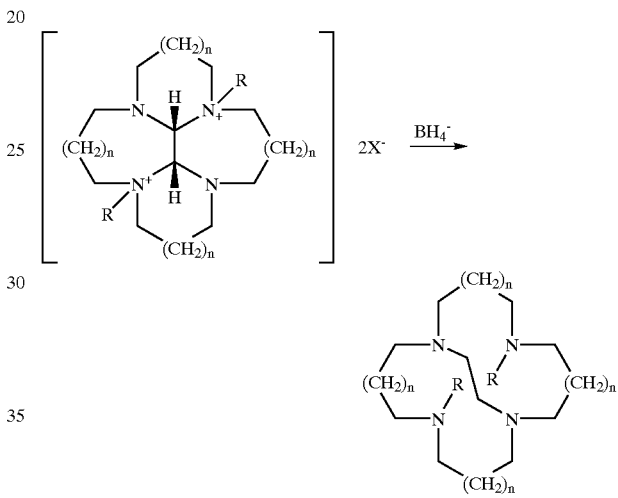

wherein the cis-tetracycle bis quaternary salt is converted to the cross-bridged tetraaza macrocycle.

The pH under which Step (a) must be conducted is at least 11, preferably at least 12. Preferably the base which is used to adjust the pH is in the form of an aqueous solution. Preferred bases are selected from the group consisting of potassium carbonate, sodium carbonate, sodium hydroxide, potassium hydroxide, and mixtures thereof. It is satisfactory to use a sufficient amount of 1 M (molar) aqueous base to adjust the pH to the required level. A convenient and preferred base is potassium carbonate.

Preferably Step (a) is conducted in the presence of a solvent. Non-limiting examples of solvents include benzene, toluene, methanol, ethanol, n-propanol, isopropanol, diethyl ether, tetrahydrofuran, and mixtures thereof; prefered solvents are selected from the group consisting of ethanol, n-propanol, isopropanol, and mixtures thereof. When a solvent is present and the base is in the form of an aqueous solution, the ratio of said volume of aqueous base, preferably 1 molar aqueous base, to said solvent is from about 1:10 to about 1:1, preferably the ratio of the volume of aqueous base to solvent is 1:4. It is desirable, but not a requirement, that the aqueous base and solvent form a two phase system.

The reducing agent for the process of the present invention is borohydride, $BH_4^-$. Non-limiting examples of reducing agents which are preferred for the process of the present invention include reducing agents having the formula $MBH_4$ wherein M is selected from the group consisting of lithium, sodium, potassium, and mixtures thereof; preferably M is sodium (sodium borohydride). Surprisingly, under the conditions of the present process, only the stoichiometrically required 1 mole equivalent of sodium borohydride (corresponding to two moles of $H_2$) is needed to accomplish the desired transformation. However, up to 3.5 mole equivalents can be suitably used, especially in continuous processes wherein the aqueous phase is recycled and the amount of reducing agent which is consumed during the chemical ring cleavage is replace prior to introduction of another batch of starting material. A preferred embodiment, which balances time, reaction temperature, and yield, uses 2 mole equivalents of borohydride reducing agent. This limitation removes the need for large amounts of acid to destroy the unused borohydride, thereby eliminating the unnecessary release of excess hydrogen gas during work-up and optional isolation.

Step (a) may be conducted at any temperature from about 10° C., preferably from about room temperature, more preferably from about 40° C. to about 70° C., more preferably to about 50° C.

In a preferred embodiment of the process of the present invention, sufficient 1 M base is admixed with ethanol in a suitable reaction vessel to form a two phase system which is mechanically stirred and warmed to about 50° C. Concurrently and in a portion-wise manner over equal time intervals, 2 equivalents of sodium borohydride and a cis tetracycle are added to the reaction vessel maintaining the temperature at about 50° C. After addition of the reagents is complete, the reaction is monitored using any convenient means, for the consumption of the cis-tetracycle. Once the starting material is consumed the organic phase is decanted and the product isolated by normal procedures.

The following is a non-limiting example of the process of the present invention used to fragment a specific tetracycle.

EXAMPLE 1

Preparation of 5,12-dimethyl-1,5,8,12-tertaaza-bicyclo[6.6.2]hexadecane

Distilled water (25 mL) and potassium carbonate (13.8 g) are combined in a 250 mL round bottomed flask. Absolute ethanol (75 mL) is added and the resulting two phase solution is stirred and heated to about 60° C. Sodium borohydride (1.60 g., 42.3 mmol) and the cis-tetracycle having the formula:

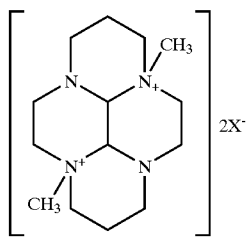

wherein X is methylsulfate, (10.0 g, 21.1 mmol) is added to the solution. The reaction is stirred at 60° C. for 75 minutes. The reaction mixture is transferred to a separatory funnel and the ethanol layer collected. The ethanol is evaporated under reduced pressure and affords a tan-colored oily solid. The crude material is treated with 5N KOH (5 mL) until dissolved and the aqueous solution extracted with toluene (2×50 mL). The toluene is removed in vacuo to afford a crude oil which is subsequently distilled at about 0.2 mm Hg to yield 5.2 g (95%) of 5,12-dimethyl-1,5,8,12-tertaaza-bicyclo[6.6.2]hexadecane as a colorless oil.

What is claimed is:

1. A process for preparing a tetraaza macrocyclic ligand having the formula:

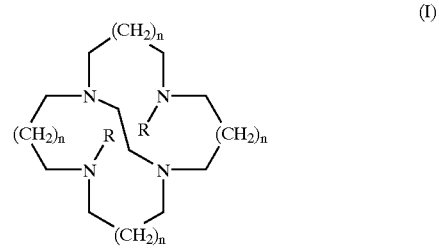

(I)

wherein each R is independently $C_1$–$C_{22}$ linear alkyl, $C_1$–$C_{22}$ branched alkyl, $C_7$–$C_{22}$ alkylenearyl, $C_8$–$C_{22}$ alkyl substituted alkylenearyl, and mixtures thereof; each index n is independently from 0 to 3, said process comprising the steps of:

a) reacting one mole equivalent of a tetraaza macrocyclic ligand precursor having the formula:

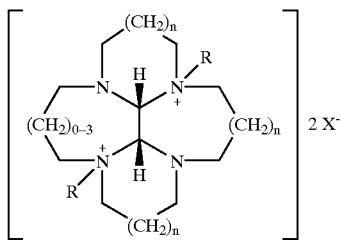

wherein $X^-$ is an anion which provides charge neutrality, with from 1 mole equivalent to 3 mole equivalents a reducing agent having the formula $MBH_4$ wherein M is selected from the group consisting of lithium, sodium, potassium, and mixtures thereof; at a pH of at least 11 to form a macrocyclic ligand; and b) optionally isolating said macrocyclic ligand.

2. A process according to claim 1 wherein R is $C_1$–$C_8$ linear alkyl, $C_7$–$C_{10}$ alkylenearyl, $C_8$–$C_{10}$ alkyl substituted alkylenearyl, and mixtures thereof.

3. A process according to claim 1 wherein R is $C_1$–$C_4$ linear alkyl, benzyl, and mixtures thereof.

4. A process according to claim 3 wherein R is methyl.

5. A process according to claim 4 wherein two of the indices n are equal to 0 and two of the indices n are equal to 1.

6. A process according to claim 5 wherein said tetraaza macrocyclic ligand formed by said process has the formula:

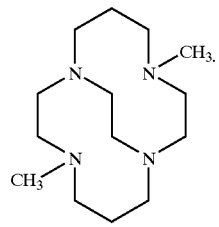

7. A process according to claim 6 wherein said reducing agent is $NaBH_4$.

8. A process according to claim 7 wherein said reducing agent is present in the amount of 2 mole equivalents.

9. A process according to claim 8 wherein said pH of step (a) is at least 12.

10. A process according to claim 9 wherein step (a) is conducted in the presence of one or more solvents.

11. A process according to claim 10 wherein step (a) is conducted in the presence of water and one or more solvents.

12. A process for preparing a tetraaza macrocyclic ligand having the formula:

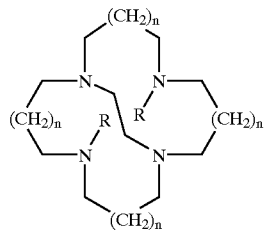

wherein R is $C_1$–$C_{22}$ linear alkyl, $C_1$–$C_{22}$ branched alkyl, $C_7$–$C_{22}$ alkylenearyl, $C_8$–$C_{22}$ alkyl substituted alkylenearyl, and mixtures thereof; each index n is independently from 0 to 3, said process comprising the steps of:

a) combining in a reaction vessel a one molar solution of base and a solvent, wherein the ratio of said base to said solvent is from 1:10 to 1:1; to form a two phase solution;

b) adding to said two phase solution one mole equivalent of a tetraaza macrocyclic ligand precursor having the formula:

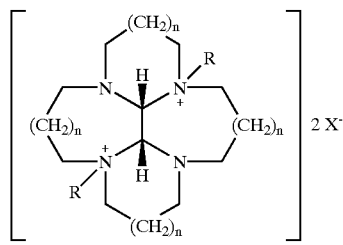

wherein $X^-$ is an anion which provides charge neutrality, and from 1 mole equivalent to 3 mole equivalents of a reducing agent having the formula $MBH_4$ wherein M is selected from the group consisting of lithium, sodium, potassium, and mixtures thereof; at a pH of at least 11 to form a macrocyclic ligand;

c) separating the aqueous and non-aqueous phases; and d) optionally isolating said macrocyclic ligand.

13. A process for preparing a tetraaza macrocyclic ligand having the formula:

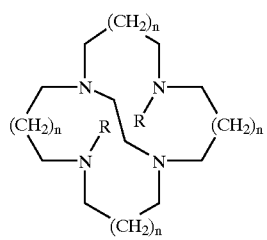

wherein R is $C_1$–$C_{22}$ linear alkyl, $C_1$–$C_{22}$ branched alkyl, $C_7$–$C_{22}$ alkylenearyl, $C_8$–$C_{22}$ alkyl substituted alkylenearyl, and mixtures thereof; each index n is independently from 0 to 3, said process comprising the steps of:

a) combining in a reaction vessel a one molar solution of base, said base selected from the group consisting of potassium carbonate, sodium carbonate, sodium hydroxide, potassium hydroxide, and mixtures thereof; and a solvent, said solvent selected from the group consisting of benzene, toluene, methanol, ethanol, n-propanol, isopropanol, diethyl ether, tetrahydrofuran, and mixtures thereof; wherein the ratio of said base to said solvent is from 1:10 to 1:1; to form a two phase solution;

b) adding to said two phase solution, at a temperature of from 10° C. to 70° C., a tetraaza macrocyclic ligand precursor having the formula:

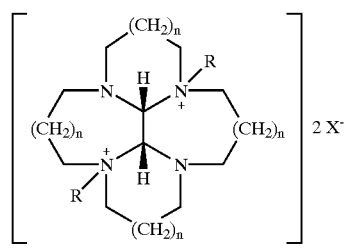

wherein $X^-$ is an anion which provides charge neutrality, with from 1 mole equivalent to 3 mole equivalents a reducing agent having the formula $MBH_4$ wherein M is selected from the group consisting of lithium, sodium, potassium, and mixtures thereof; at a pH of at least 11 to form a macrocyclic ligand;

c) separating the aqueous and non-aqueous phases; and d) optionally isolating said macrocyclic ligand from said non-aqueous phase.

14. A process for preparing 5,12-dimethyl-1,5,8,12-tertaaza-bicyclo[6.6.2]hexadecane having the formula:

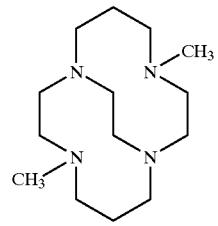

said process comprising the steps of:

a) combining in a reaction vessel a one molar solution of base, said base selected from the group consisting of potassium carbonate, sodium carbonate, and mixtures thereof; and a solvent, said solvent selected from the group consisting of ethanol, n-propanol, isopropanol, and mixtures thereof; wherein the ratio of the volume of said base to said volume of solvent is 1:4; to form a two phase solution comprising an aqueous phase and a solvent phase;

b) adding to said two phase solution, at a temperature of from 50° C., a macrocyclic ligand precursor having the formula:

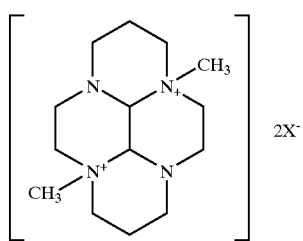
2X⁻
wherein X⁻ is an anion which provides charge neutrality, together with 2 mole equivalents of NaBH$_4$ at a pH of at least 12 to form 4,11-dimethyl-1,4,8,11-tetraaza-bicyclo[6.6.2]hexadecane;
c) separating from said two phase system said solvent phase; and
d) isolating from said solvent phase 5,12-dimethyl-1,5,8,12-tertaaza-bicyclo[6.6.2]hexadecane.
* * * * *